(12) United States Patent
Yuan

(10) Patent No.: US 11,134,855 B2
(45) Date of Patent: Oct. 5, 2021

(54) OPTOELECTRONIC SENSOR, CONTROL METHOD FOR OPTOELECTRONIC SENSOR, AND PULSE MONITOR INCLUDING OPTOELECTRONIC SENSOR

(71) Applicant: BOE TECHNOLOGY GROUP CO., LTD., Beijing (CN)

(72) Inventor: Zuo Yuan, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 443 days.

(21) Appl. No.: 15/573,880

(22) PCT Filed: May 11, 2017

(86) PCT No.: PCT/CN2017/083921
§ 371 (c)(1),
(2) Date: Nov. 14, 2017

(87) PCT Pub. No.: WO2018/064891
PCT Pub. Date: Apr. 12, 2018

(65) Prior Publication Data
US 2018/0344180 A1   Dec. 6, 2018

(30) Foreign Application Priority Data

Oct. 9, 2016   (CN) .......................... 201610881246.3

(51) Int. Cl.
*A61B 5/00* (2006.01)
*A61B 5/024* (2006.01)
*A61B 5/1495* (2006.01)

(52) U.S. Cl.
CPC ........ *A61B 5/02427* (2013.01); *A61B 5/1495* (2013.01); *A61B 5/7214* (2013.01);
(Continued)

(58) Field of Classification Search
CPC   A61B 5/02427–02433; A61B 5/02444; A61B 5/14552; A61B 5/7214;
(Continued)

(56) References Cited

U.S. PATENT DOCUMENTS

2002/0173706 A1* 11/2002 Takatani ............ A61B 5/14552
600/323
2003/0018274 A1   1/2003 Takahashi et al.
(Continued)

FOREIGN PATENT DOCUMENTS

CN   104224144 A   12/2014
CN   104586370 A   5/2015
(Continued)

OTHER PUBLICATIONS

English translation of International Search Report dated May 11, 2017, issued in counterpart International Application No. PCT/CN2017/083921 (14 pages).
(Continued)

*Primary Examiner* — Jonathan Cwern
*Assistant Examiner* — Amal Aly Farag
(74) *Attorney, Agent, or Firm* — Westerman, Hattori, Daniels & Adrian, LLP

(57) ABSTRACT

An optoelectronic sensor, a control method for the optoelectronic sensor, and a pulse monitor including the optoelectronic sensor. The optoelectronic sensor may include a light source, a first receiver, a second receiver, and a phantom material layer that is facing a light-emitting side of the light source and at least partially overlapping with the second receiver.

17 Claims, 7 Drawing Sheets

(52) U.S. Cl.
CPC ............ *A61B 2560/0223* (2013.01); *A61B 2560/0233* (2013.01); *A61B 2560/0238* (2013.01); *A61B 2562/0238* (2013.01)

(58) Field of Classification Search
CPC .......... A61B 5/1495; A61B 2560/0238; A61B 2560/0233; A61B 2560/0223; A61B 2562/0238; A61B 5/0064; A61B 5/02; A61B 5/7207; A61B 5/7235
See application file for complete search history.

(56) References Cited

U.S. PATENT DOCUMENTS

| | | | | |
|---|---|---|---|---|
| 2006/0114003 | A1* | 6/2006 | Onishi | G01R 29/0885 324/632 |
| 2013/0116603 | A1* | 5/2013 | Nita | A61N 7/00 601/2 |
| 2016/0270676 | A1* | 9/2016 | Yamashita | A61B 5/02427 |
| 2017/0112448 | A1 | 4/2017 | Liu et al. | |
| 2018/0353134 | A1* | 12/2018 | Walter | A61B 5/14551 |
| 2019/0090801 | A1* | 3/2019 | Rogers | A61B 5/4064 |

FOREIGN PATENT DOCUMENTS

| | | |
|---|---|---|
| CN | 104706336 A | 6/2015 |
| CN | 204797827 U | 11/2015 |
| CN | 105266773 A | 1/2016 |
| CN | 106333657 A | 1/2017 |
| EP | 3 061 387 A1 | 8/2016 |
| EP | 3 106 086 A1 | 12/2016 |
| JP | 2008-161492 A | 7/2008 |

OTHER PUBLICATIONS

Office Action dated Jul. 4, 2017, issued in counterpart Chinese Application No. 201610881246.3, with English translation (12 pages).

* cited by examiner

OPTOELECTRONIC SENSOR, CONTROL METHOD FOR OPTOELECTRONIC SENSOR, AND PULSE MONITOR INCLUDING OPTOELECTRONIC SENSOR

CROSS-REFERENCE TO RELATED APPLICATIONS

This application claims the benefit of the filing date of Chinese Patent Application No. 201610881246.3 filed on Oct. 9, 2016, the entire disclosure of which is hereby incorporated by reference.

TECHNICAL FIELD

The present disclosure relates generally to optoelectronic technologies, and in particular, to an optoelectronic sensor, a control method for the optoelectronic sensor, and a pulse monitor including the optoelectronic sensor.

BACKGROUND

The heart's alternate expansion and contraction create a corresponding contraction and expansion in the arteries. This cyclical action produces a blood pressure maximum at systole, called systolic pressure, and a minimum pressure at diastole, called diastolic pressure. Each systole starts a new pulse that proceeds as a wave of expansion throughout the arteries, and is known as the pulse wave. The pulse wave is the strongest at the common carotid artery in the neck, and dissipates as it travels throughout the circulatory system. Parameters of the blood pulse, including pulse waveform, strength, velocity, and rhythm, can be valuable gauges of a person's cardiovascular and general health. As such, blood pulse has long been recognized as an important physiological parameter.

BRIEF SUMMARY

One embodiment of the present disclosure is an optoelectronic sensor for determining a blood pulse. The optoelectronic sensor may comprise a base substrate; a light source on the base substrate; a first receiver on the base substrate and on one side of the light source; a second receiver on the base substrate and on a different side of the light source from the first receiver; and a phantom material layer facing a light-emitting side of the light source and at least partially overlapping with the second receiver. The first receiver may be configured to generate a first photo signal based on a light emitted from the light source and reflected from a skin of a user, and convert the first photo signal into a first electrical signal. The second receiver may be configured to generate a second photo signal based on a light emitted from the light source and reflected from the phantom material layer, and convert the second photo signal into a second electrical signal. The optoelectronic sensor may be configured to, in determining the blood pulse, apply a compensation factor to the first electrical signal based on the second electrical signal.

In at least some embodiments, an optoelectronic sensor according to the present disclosure may further comprise a processor coupled to the first receiver and the second receiver. The processor may be configured to invert the second electrical signal, and add the first electrical signal and the inverted second electrical signal, so as to generate a blood pulse signal for determining the blood pulse. The inverted second electrical signal may define the compensation factor. In at least some embodiments, the processor may be configured to adjust a baseline of the blood pulse signal generated by the processor, and to adjust a baseline of a blood pulse waveform determined from the blood pulse signal.

In at least some embodiments, a phantom material layer in an optoelectronic sensor according to the present disclosure may face an entirety of a light-receiving surface of the second receiver. A width of the phantom material layer may be less than half of an overall width of the optoelectronic sensor.

In at least some embodiments, an optoelectronic sensor according to the present disclosure may further comprise a first light-blocking layer on a side of the phantom material layer distal to the second receiver.

In at least some embodiments, an optoelectronic sensor according to the present disclosure may further comprise a transparent housing containing the light source, the first receiver, the second receiver, and the phantom material layer. A first separation distance may separate a light-receiving surface of the first receiver and a side of the transparent housing facing the light-receiving surface of the first receiver. A second separation distance may separate a light-receiving surface of the second receiver from a side of the transparent housing facing the light-receiving surface of the second receiver. The first separation distance may be larger than the second separation distance.

In at least some embodiments, a phantom material layer in an optoelectronic sensor according to the present disclosure may be on a side of the transparent housing facing the second receiver. The first light-blocking layer may be between the phantom material layer and the transparent housing.

In at least some embodiments, a light source in an optoelectronic sensor according to the present disclosure may be between the first receiver and the second receiver. The light source, the first receiver and the second receiver may be arranged substantially along a same direction. The light source may be at a halfway point between the first receiver and the second receiver.

In at least some embodiments, an optoelectronic sensor according to the present disclosure may further comprise a second light-blocking layer on at least one side surface of the light source facing one of the first receiver and the second receiver.

In at least some embodiments, a phantom material layer in an optoelectronic sensor according to the present disclosure may be configured to mimic the skin of the user. The phantom material layer may have a thickness of from 1 to 2 millimeters. The phantom material layer may be formed by solidifying a liquid mixture comprising a gelling agent, deionized water, saline solution, and oil into a gel material.

In at least some embodiments, at least one of a first receiver and a second receiver in an optoelectronic sensor according to the present disclosure may be a photosensitive element. In at least some embodiments, at least one of the first receiver and the second receiver may be a photodiode.

Another embodiments of the present disclosure is a method for determining a blood pulse using an optoelectronic sensor comprising a base substrate, a light source on the base substrate, a first receiver on the base substrate, a second receiver on a base substrate and on a different side of the light source from the first receiver, a phantom material layer facing a light-emitting side of the light source and at least partially overlapping with the second receiver. The method may comprise generating a first photo signal based on a light emitted from the light source and reflected by a skin of a user; converting the first photo signal into a first electrical signal; generating a second photo signal based on a light emitted from the light source and reflected by the phantom material layer; converting the second photo signal into a second electrical signal; and applying a compensation factor to the first electrical signal based on the second electrical signal. In at least some embodiments, the applying of the compensation factor may comprise inverting the second electrical signal, and adding the inverted second electrical signal to the first electrical signal, so as to generate a blood pulse signal for determining the blood pulse. The inverted second electrical signal may define the compensation factor.

In at least some embodiments, a method for determining a blood pulse according to the present disclosure may further comprise adjusting a baseline of the blood pulse signal, and adjusting a baseline of a blood pulse waveform determined from the blood pulse signal.

Another embodiment of the present disclosure is a pulse monitor. The pulse monitor may comprise an optoelectronic sensor as described above.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings, in which:

DETAILED DESCRIPTION

Next, the embodiments of the present disclosure will be described clearly and completely in conjunction with the accompanying drawings, which are described briefly above. The subject matter of the present disclosure is described with specificity to meet statutory requirements. However, the description itself is not intended to limit the scope of this disclosure. Rather, the inventors have contemplated that the claimed subject matter might also be embodied in other ways, to include different steps or elements similar to the ones described in this document, in conjunction with other present or future technologies.

While the present technology has been described in connection with the embodiments of the various figures, it is to be understood that other similar embodiments may be used or modifications and additions may be made to the described embodiment for performing the same function of the present technology without deviating therefrom. Therefore, the present technology should not be limited to any single embodiment, but rather should be construed in breadth and scope in accordance with the appended claims. In addition, all other embodiments obtained by one of ordinary skill in the art based on embodiments described in this document are considered to be within the scope of this disclosure.

Figure 1:
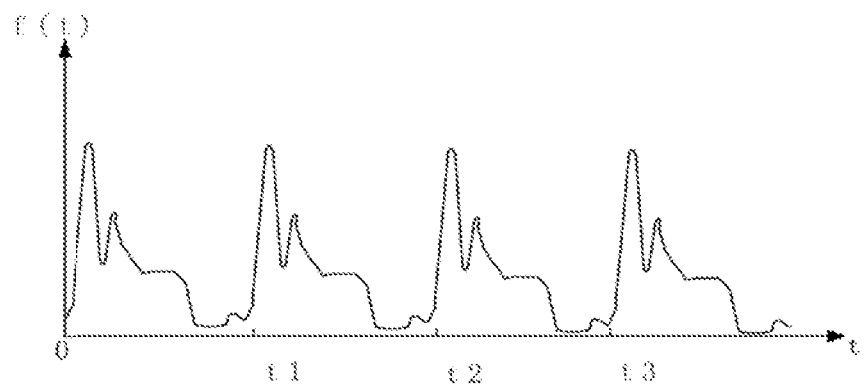
FIG. 1 shows blood pulse signals determined from a related photoplethysmograph system.

The importance of blood pulse has spurred the development of numerous methods of monitoring and evaluating it. Among existing technologies, optoelectronic-type sensors are advantageous and popular in that they provide rapid responses, have high sensitivity, require simple construction, and are generally reliable. Optoelectronic-type sensors use light for determining and registering variations in a user's blood pulse. The sensors operate on the basic principle that when the user's blood volume changes, the amount of light absorption by the surrounding tissues undergo corresponding changes. By detecting these changes in light absorption, the sensors can determine and evaluate the basic characteristics of the user's blood pulse. Photoplethysmography (PPG) is an example of an optoelectronic sensor, and can be used to measure variations in the frequency, shape, and amplitude of the user's blood pulse. FIG. 1 shows an example of a photoplethysmogram.

Figure 2:
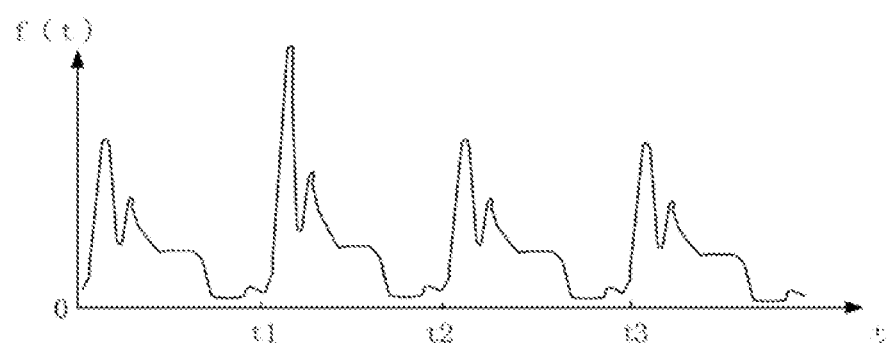
FIG. 2 shows distortions in the blood pulse signals determined from a related photoplethysmograph system as a result of an external interference at time t1.

However, while the related photoplethysmograph systems are useful, they have disadvantages. For example, when measuring blood pulse, an external interference such as a movement in a user's arm may interfere with a sensor's data gathering, and cause distortions in the blood pulse being measured. The effects are illustrated in FIG. 2. As shown in FIG. 2, the sensor experiences an external interference at time t1, and a blood pulse of distortedly large amplitude is registered as a result. The external interference was eliminated at time t2, and the blood pulse returned to normal. A comparison of FIGS. 1 and 2 highlight the distorting effects of external disturbances on the blood pulses being registered, which effects can limit the measurement accuracy and sensitivity of the sensor. In view of the foregoing, there exists a need to develop a sensor system that reduces distortions as a result of external interferences and improves the anti-interference ability to the movement.

Figure 3A:
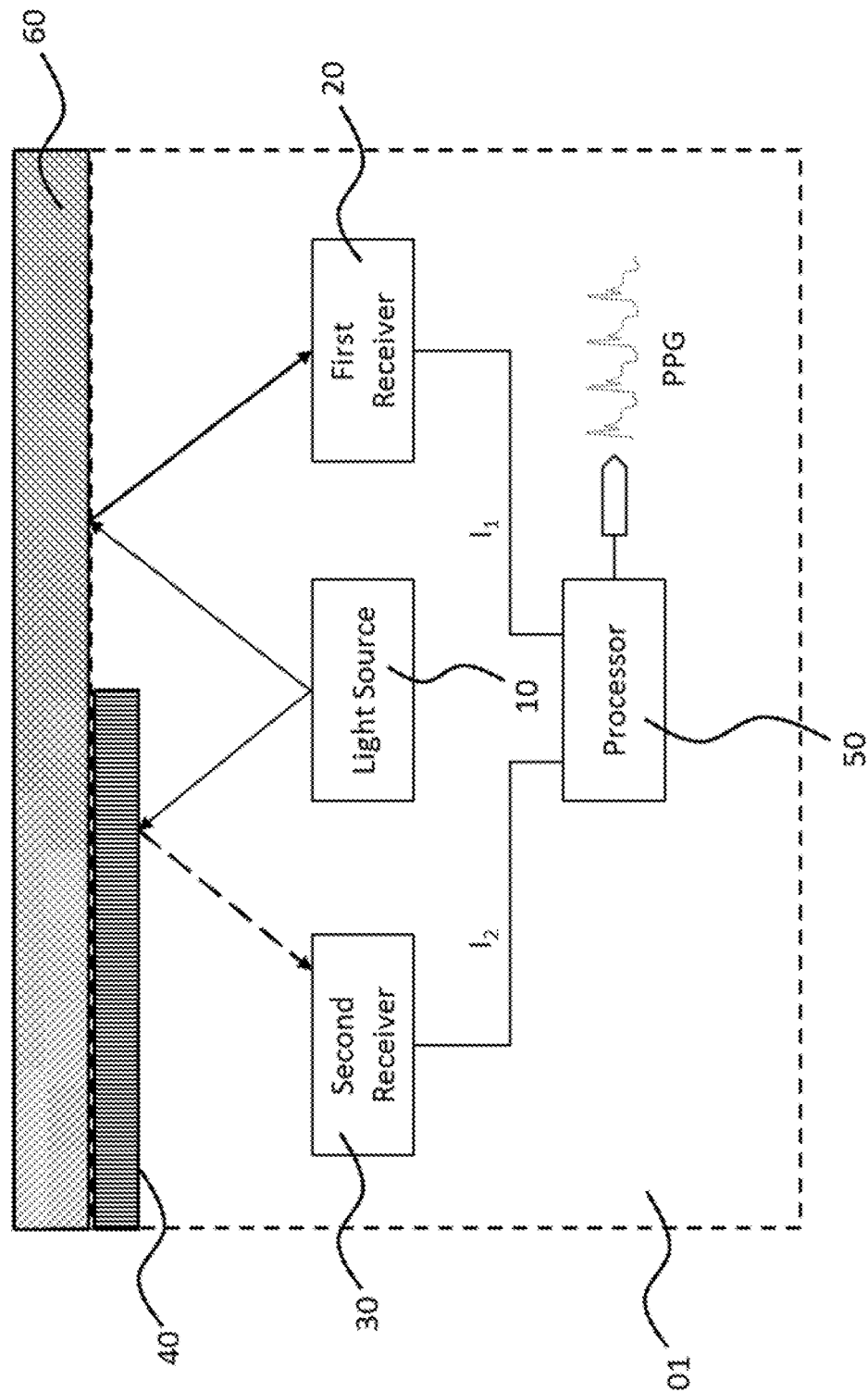
FIG. 3a shows a schematic diagram of an optoelectronic sensor according to an embodiment of the present disclosure.

FIG. 3a shows a schematic diagram of an optoelectronic sensor according to an embodiment of the present disclosure. The optoelectronic sensor 01 comprises a light source 10, a first receiver 20, a second receiver 30, and a phantom material layer 40. Optionally, the light source 10 in an optoelectronic sensor 01 according to the present disclosure is a light-emitting diode (LED). Optionally, the light emitted from the light source 10 is green light, red light, or infrared light.

The phantom material layer 40 is positioned to face a light-emitting side of the light source 10. The phantom material layer 40 may be positioned to face, or at least partially overlap with, the second receiver 30. Optionally, the phantom material layer 40 may be positioned to face, or at least partially overlap with, a light-receiving surface of the second receiver 30 (that is, the side of the second receiver 30 receiving light reflected by the phantom material layer 40).

A first portion of the light emitted from the light source 10 is reflected along a first light path (indicated in FIG. 3a by the thick solid arrow) by the skin 60 of the user of the optoelectronic sensor 01. More particularly, as shown in FIG. 3a, light is reflected by the portion of the user's skin 60 above the first receiver 20. The first receiver 20 is exposed to the skin 60 of the user.

A second portion of the light emitted from the light source 10 is reflected along a second light path (indicated in FIG. 3a by the dotted arrow) by the phantom material layer 40, which is shown in FIG. 3a as being located above the second receiver 30.

It should be noted that the terms of direction and/or orientation, such as "above" and "below", do not have fixed definitions, and are used only to facilitate the description of the relative positions of different structures. The terms may be assigned according to how the optoelectronic sensor 01 is applied to the skin 60 of the user.

Optionally, to maximize the amount of reflected light from the phantom material layer 40 that is received by the second receiver 30, the phantom material layer 40 faces an entirety of the light-receiving surface of the second receiver 30. From the perspective of the second receiver 30, at any point on the light-receiving surface of the second receiver 30, the light-receiving surface faces the phantom material layer. For example, depending on the dimensions of the second receiver 30 in the optoelectronic sensor 01, the phantom material layer 40 may have a surface area of 2 mm×2 mm, or 3 mm×3 mm. The dimensions of the phantom material layer 40 are not particularly limited, and may be adjusted according to the dimensions of the light-receiving surface of the second receiver 30. Optionally, the surface of the phantom material layer 40 facing the second receiver 30 has a surface area that is larger than the surface area of the light-receiving surface of the second receiver 30, so that the surface of the phantom material layer 40 can cover an entirety of the light-receiving surface of the second receiver 30.

The phantom material layer 40 is a layer of artificial tissue formulated to mimic closely the electrical properties (for example, conductivity and/or dielectric constant) of human tissues (for example, human skin). The phantom material layer 40 may be prepared as follows. Appropriate proportions of a gelling agent (for example, gelatin, agar, and the like), deionized water, saline solution, oil, fat, and/or other suitable additives are thoroughly mixed to obtain a substantially uniform liquid. The liquid mixture is then allowed to cool for approximately 7 to 10 days, so that the liquid mixture can gelatinize into a semi-solid or gel material. The gel material is then sliced into thin layers having a thickness in the range of approximately 1 to 2 millimeters (mm), so as to obtain a phantom material layer 40 suitable for use in an optoelectronic sensor according to the present disclosure.

Tissues of different human body parts exhibit different electrical properties. For example, tissues from fingertips, arms, earlobes, forehead, and other parts of the human body exhibit different conductivities and/or dielectric constants. Accordingly, the composition of the phantom material layer 40 may be adjusted as appropriate to obtain the electrical properties of the part of the body being mimicked. The human tissues that the phantom material layer 40 may mimic are not particularly limited, and the phantom material layer 40 may mimic any human tissue according to the desired application(s) of the optoelectronic sensor.

Next, the operation of an optoelectronic sensor according to the present disclosure will be described.

A first portion of the light emitted from the light source 10 is reflected along a first light path (as indicated by the dotted arrow in FIG. 3a) by the skin 60 of the user. The reflected light impinges on the first receiver 20. The first receiver 20 is configured to generate a first photo signal based on a light emitted from the light source and reflected from a skin of a user, and convert the first photo signal into a first electrical signal $I_1$.

A second portion of the light emitted from the light source 10 is reflected along a second light path (as indicated by the thick solid arrow in FIG. 3a) by the phantom material layer 40. The reflected light impinges on the second receiver 30. The second receiver 30 is configured to generate a second photo signal based on a light emitted from the light source and reflected from the phantom material layer, and convert the second photo signal into a second electrical signal $I_2$.

The first receiver 20 and the second receiver 30 may each be a photosensitive element. A photosensitive element may be a photodiode, a photosensitive transistor, a photoresistor, silicon photovoltaic cell, and the like. In at least some embodiments, the photosensitive element is a photodiode.

The optoelectronic sensor 01 may further comprise a processor 50 coupled to the first receiver 20 and the second receiver 30. The processor 50 may be a microprocessor, a digital signal processor, an application specific integrated circuit, a field programmable gate array, any suitable programmable logic device, discrete gate or transistor logic, discrete hardware components, or any combination thereof, which may be designed to perform the functions described herein. That is, there are no particular limitations on the implementation forms of the processor 50. As shown in FIG. 3a, the processor 50 is configured to receive the first electrical signal $I_1$ and the second electrical signal $I_2$. The processor 50 is configured to apply a negative compensation to the first electrical signal $I_1$ based on the second electrical signal $I_2$. Accordingly, in at least some embodiments, the optoelectronic sensor 01 is a reflectance optoelectronic sensor.

Figure 4A:
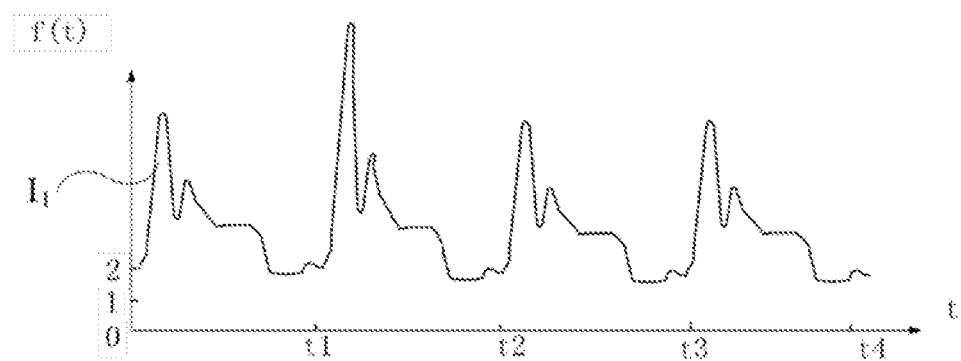
FIG. 4a shows a distorting effect of external interference on an electrical signal generated by the first receiver in the optoelectronic sensor illustrated in FIG. 3b.

When a user uses an optoelectronic sensor 01, an external interference (for example, the user's arm movement to bring the optoelectronic sensor into a viewable position) may interfere with and distort the data being registered by the sensor. The distortion may manifest itself in the first electric signal $I_1$. For example, as shown in FIG. 4a, the optoelectronic sensor 01 experiences an external interference at time t1, causing an instantaneous distortion in the first electrical signal $I_1$ in the form of a blood pulse having abnormally large amplitude. When the external interference is removed at time t2, the amplitude of the blood pulse returns to normal. The term "normal" is used here to refer to the usual blood pulse of the user.

The first electrical signal $I_1$ is obtained by an optoelectronic conversion in the first receiver 20 of light reflected from the user's skin 60. When light emitted from the light source 10 penetrates the skin 60 and then reflected, the light reaching the first receiver 20 has already been modulated by artifacts in the user's skin and blood, for example, by bone tissues, interstitial fluid, and blood hemoglobin. Blood hemoglobin concentration has been observed to undergo pulsatile variations, whereas bone tissues and interstitial fluid generally do not change with arterial pulsatile flow. Therefore, the first electrical signal $I_1$ can be separated into at least two components: the time-varying "alternating current (AC)" component of the signal that is related to the beat-to-beat variations caused by the pulsation and flow of blood in the arteries, and the slow-varying or unchanging "direct current (DC)" component of signal that is related to other physiological and physical properties (for example, non-pulsatile arterial blood, pulsatile and non-pulsatile venous blood, tissues, and bones). The terms "AC component" and "DC component" are used to describe the anatomical and physiological components responsible for generating the blood pulse signal (i.e., the AC component) and the components responsible for attenuating the signal (i.e., the DC component).

Figure 4B:
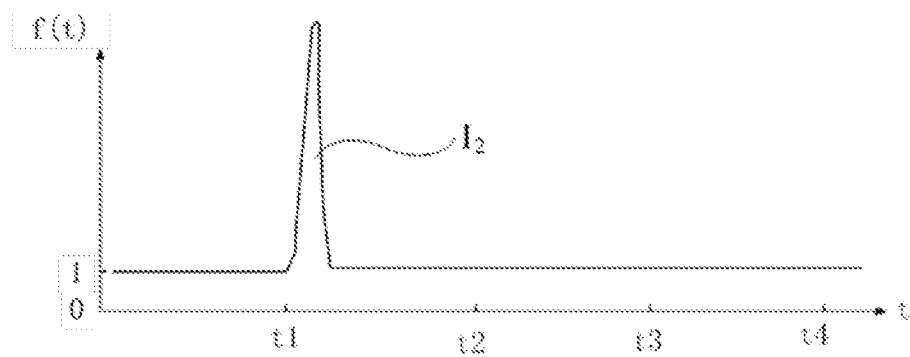
FIG. 4b shows a distorting effect of external interference on an electrical signal generated by the second receiver in the optoelectronic sensor illustrated in FIG. 3b.

An external interference that distorts the first electrical signal $I_1$ can also distort the second electrical signal $I_2$. For example, as shown in FIG. 4b, the external interference at time t1 also causes an instantaneous distortion in the second electrical signal $I_2$, in the form of an abnormal spike in the blood pulse data. When the external interference is removed at time t2, the amplitude of the blood pulse returns to normal. Here also, the term "normal" is used here to refer to the usual blood pulse of the user.

The second electrical signal $I_2$ is obtained by an optoelectronic conversion in the second receiver 30 of light reflected from the phantom material layer 40. When light emitted from the light source 10 impinges on the phantom material layer 40, interaction of the light with components making up the phantom material layer 40 is expected to modulate the light before it is reflected. However, the proportions of the components are fixed, so that the amount of light absorbed or reflected by the phantom material layer 40 is substantially fixed, and does not vary to any meaningful extent according to the pulsatile flow of blood in the arteries. Therefore, the second electrical signal $I_2$ may comprise predominantly a DC component.

Figure 4C:
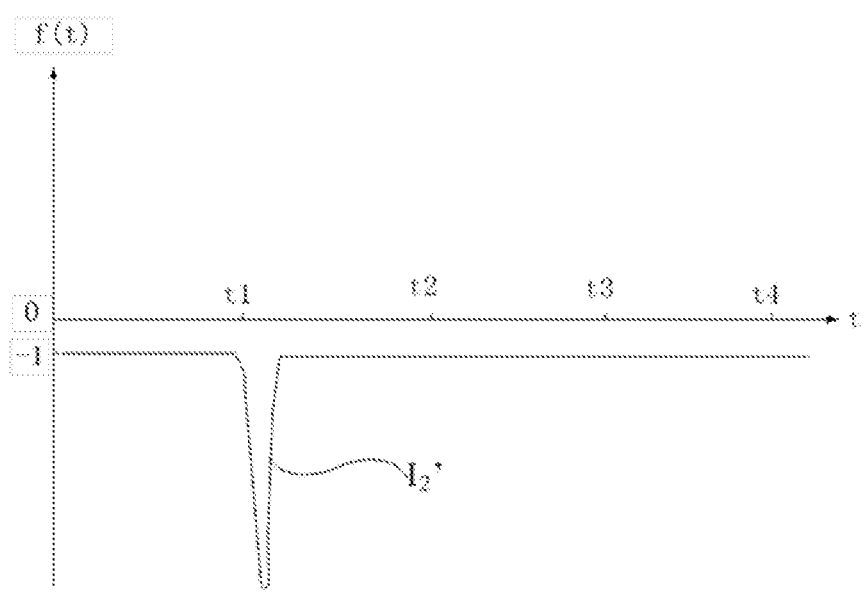
FIG. 4c shows the electrical signal in FIG. 4a, after a 180° inversion.
Figure 4D:
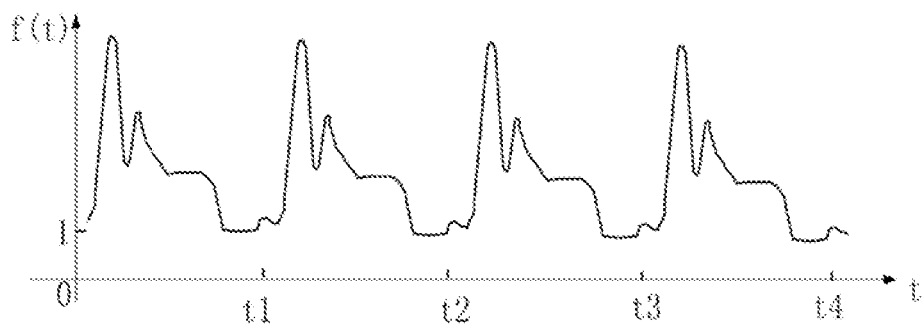
FIG. 4d shows the blood pulse signals generated by the processor in the optoelectronic sensor illustrated in FIG. 3a, after the distorting effect of the external interference has been removed.

The processor 50 is configured to apply a negative compensation to the first electrical signal $I_1$. More particularly, the processor is configured to invert the second electrical signal $I_2$ (for example, as shown in FIG. 4c), and then to add the inverted second electrical signal $I_2'$ to the first electrical signal $I_1$. The inverted second electrical signal $I_2'$ may thus define a compensation factor for the negative compensation. The processor 50 is thus configured to subtract the distortion caused by the external interference from the first electrical signal $I_1$ by an amount of distortion in the second electrical signal $I_2$. The processor 50 outputs a blood pulse signal from which the distortions caused by the external interference have been removed (for example, as shown in FIG. 4d). The present disclosure thus makes it possible to design an optoelectronic sensor 01 in which the probability of distortions in the blood pulse data is minimized, and the measurement accuracy and sensitivity of the optoelectronic sensor 01 increased.

Figure 3B:
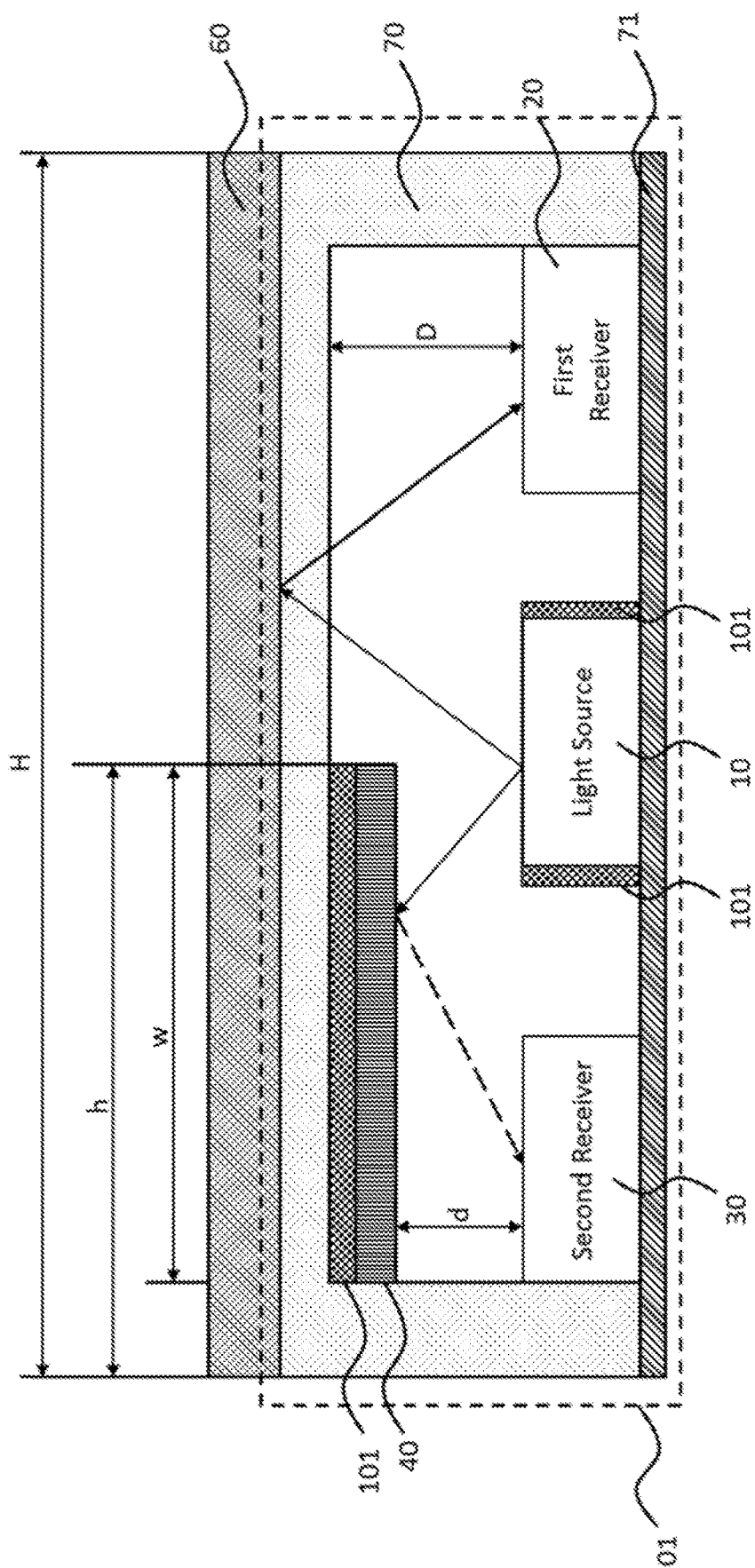
FIG. 3b shows a schematic diagram of an optoelectronic sensor according to a different embodiment of the present disclosure.

In at least some embodiments, the light source 10 in an optoelectronic sensor 01 according to the present disclosure is a light-emitting diode (LED). Optionally, as shown in FIG. 3b, the light source 10 is disposed between the first receiver 20 and the second receiver 30, so that the respective photo signals received by the first and second receivers 20, 30 are identical or nearly identical. The light emitted from the light source 10 has certain intensity. Positioning the light source 10 between the first and second receivers 20, 30 can minimize deviations in the intensity of reflected light (and therefore, the strength of the photo signals) received by the first and second receivers 20, 30, respectively. Optionally, the light source 10 is disposed at a halfway point between the first receiver 20 and the second receiver 30.

Optionally, a light-blocking layer 101 is provided at least one side of the light source 10 facing either the first receiver 20 or the second receiver 30. Optionally, the light-blocking layer 101 is provided on both the side of the light source 10 facing the first receiver 20 and the side facing the second receiver 30. The light-blocking layer 101 can prevent light emitted from the light source 10 from directly impinging on the first or second receiver 20, 30; otherwise, light pollution on the first and second receivers 20, 30 can interfere with the receivers' detection of reflected light, and compromise the conversion efficiency of the first and second receivers 20, 30. The light-blocking layer 101 may be a thin film layer composed of black-colored resin material; a thin film layer that has been subject to blackening treatment; or a plate having very low transmittance.

There are no particular limitations on the construction or composition of the light-blocking layer 101, and may be any suitable construction and/or composition known to a person of ordinary skill in the art.

In at least some embodiments, the optoelectronic sensor 01 may comprise a transparent housing 70, for example, as shown in FIG. 3b. The transparent housing 70 accommodates the light source 10, the first receiver 20, the second receiver 30, and the processor 50 (not shown in FIG. 3b), so as to avoid exposing the optoelectronic sensor 01 to environmental interferences. In at least some embodiments, the phantom material layer 40 may be adhered to a side of the transparent housing 70 facing the light-receiving surface of the second receiver 30. Meanwhile, light emitted from the light source 10 is able to transmit through the transparent housing 70 to the skin 60 of the user.

Optionally, a light-blocking layer 101 may be provided between the phantom material layer 40 and the transparent housing 70. For example, as shown in FIG. 3b, the light-blocking layer 101 is disposed on a side of the phantom material layer 40 opposite from, or distal to, the second receiver 30. The light-blocking layer 101 thus disposed can prevent light emitted from the light source 10 from transmitting through the phantom material layer 40 to the user's skin 60. This can in turn prevent artifacts in the user's skin 60 from changing the properties of the light received by the second receiver 30.

Optionally, as shown in FIG. 3b, the first receiver 20 may be positioned relative to the transparent housing so that a light-receiving surface of the first receiver 20 is positioned at a separation distance D from a side of the transparent housing 70 facing the first receiver 20. Light emitted from the light source 10 generally does not travel in a straight line. For the emitted light to reach the first receiver 20 or the second receiver 30, the light may be required to travel in complex pathways facing multiple stages of reflection, absorption, scattering, and/or other modulations. For example, the emitted light penetrates the transparent housing 70 in order to reach the user's skin 60, and the light reflected by the skin 60 then travels to the first receiver 20 (along the first light path identified by the thick solid arrow in FIG. 3b). Maintaining a separation distance D between the first receiver 20 and the transparent housing 70 can help provide sufficient propagation distance for the light. Similarly, the second receiver 30 may be positioned relative to the transparent housing so that a light-receiving surface of the second receiver 30 is positioned at a separation distance d from a side of the phantom material layer 40 facing the second receiver 30. There are no particular limitations on the separation distances D, d, and each separation distance D, d may be any values known to a person of ordinary skill in the art to be suitable for the desired application(s) for the optoelectronic sensor.

In the embodiment shown in FIG. 3b, the second receiver 30, the light source 10, and the first receiver 20 are arranged along one direction of the optoelectronic sensor 01, for example, in a transverse direction in FIG. 3b. The phantom material layer 40 has a width w in the direction in which the second receiver 30, the light source 10, and the first receiver 20 are arranged. A portion of the transparent housing 70 abuts the phantom material layer 40, and in particular, a surface of the phantom material layer 40 that is perpendicular to the surface facing the second receiver 30. The portion of the transparent housing 70 similarly has a width along the direction in which the second receiver 30, the light source 10, and the first receiver 20 are arranged.

Optionally, the width w of the phantom material layer 40 is less than half of the overall width of the optoelectronic sensor 01. Optionally, the combined width of the phantom material layer 40 and the portion of the transparent housing 70 abutting the phantom material layer 40 is half of the overall width of the optoelectronic sensor 01, for example, as shown in FIG. 3b. This combined width relative to the overall width of the optoelectronic sensor 01 may be expressed as the following formula:

$$h = \tfrac{1}{2} H$$

wherein h is the combined width of the phantom material layer 40 and the portion of the transparent housing 70 abutting the phantom material layer 40; and H is the overall width of the optoelectronic sensor 01.

To increase the accuracy of compensations for signal distortions, the distorted signals detected by the first and second receivers 20, 30 should be identical or nearly identical. This can be accomplished if the intensities of lights reaching the skin 60 and the phantom material layer 40 are identical or nearly identical. Controlling the width w of the phantom material layer 40, for example, as described above, can help maintain uniformity between lights reaching the skin 60 and the phantom material layer 40.

As described above, the processor 50 coupled to the first and second receivers 20, 30 is configured to apply a negative compensation to the first electrical signal $I_1$, based on information conveyed by the second electrical signal $I_2$. The processor is configured to invert the second electrical signal $I_2$, and then to add the inverted second electrical signal $I_2$ to the first electrical signal $I_1$, so as to subtract the distortion caused by the external interference from the first electrical signal $I_1$ by an amount of distortion in the second electrical signal $I_2$. The inverted second electrical signal $I_2'$ may thus define a compensation factor for the negative compensation. The risk of distortions in the blood pulse signals generated by the optoelectronic sensor 01 can thus be minimized, and the measurement accuracy of the optoelectronic sensor 01 increased. The processor 50 is described below.

Figure 6:
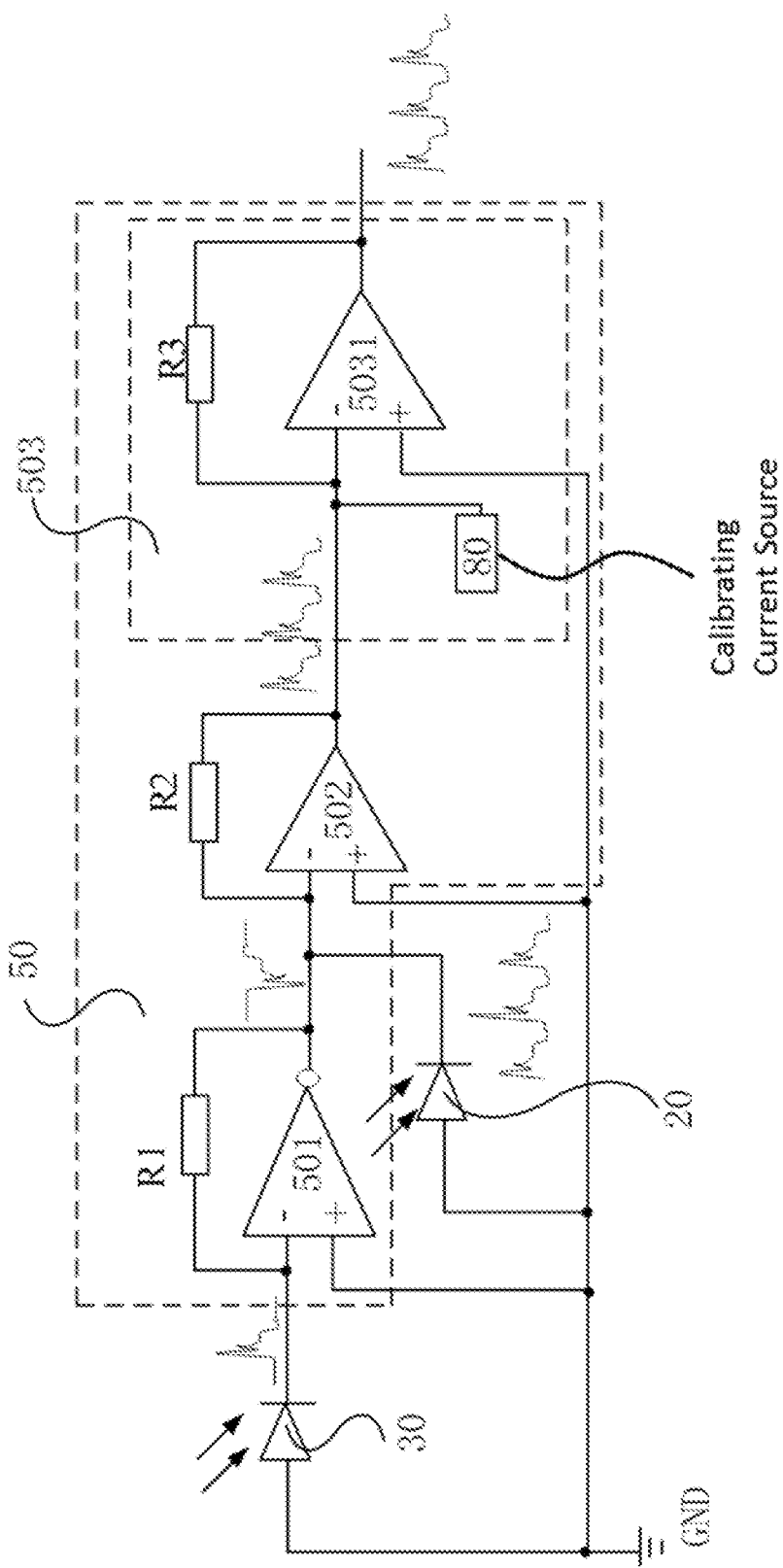
FIG. 6 shows a schematic diagram of an optoelectronic sensor according to a different embodiment of the present disclosure.

As shown in FIG. 6, the processor 50 may comprise an inverter 501. The inverter 501 comprises an inverting input end, a non-inverting end and an output end. The second receiver 30 is coupled to the inverting input end of the inverter 501. The non-inverting end of the inverter 501 is grounded (GND). The processor may 50 therefore also comprise a first adder 502. The first adder 502 comprises an inverting input end, a non-inverting end and an output end. The output end of the inverter 501 is coupled to the inverting input end of the first adder 502. The inverter 501 may also comprise a current-limiting resistor R1.

The inverter 501 is configured to invert the second electrical signal $I_2$, for example, from the state shown in FIG. 4b to the state shown in FIG. 4c. More particularly, the second electrical signal $I_2$ is inputted to the inverter 501 through the inverting input end, and following inversion by the inverter 501 (for example, by 180° as shown in FIG. 4c), is outputted from the inverter 501.

Next, the processor 50 is configured to add the inverted second electrical signal $I_2'$ to the first electrical signal $I_1$. The processor may 50 therefore also comprise a first adder 502. The first adder 502 comprises an inverting input end, a non-inverting end and an output end. The first receiver 20 is coupled to the inverting input end of the first adder 502. The non-inverting input end of the first adder 502 is grounded. The output end of the first adder 502 outputs blood pulse signals. The first adder 502 may also comprise a current-limiting resistor R2.

By adding the inverted second electrical signal $I_2'$ to the first electrical signal $I_1$, distortion in the second electrical signal $I_2$ can cancel out the distortion in the first electrical signal $I_1$. Through this negative compensation, blood pulse signals substantially free of distortions can be generated, for example, as shown in FIG. 4d.

The coordinated actions of the inversion function of the inverter 501 and the addition function of the adder 502 enable the optoelectronic sensor 50 to remove distortions in the first electrical signal $I_1$ through a negative compensation process based on information in the second electrical signal $I_2$.

As described above, the first electrical signal $I_1$ generated by the first receiver 20, for example, as shown in FIG. 4a, can be separated into at least the AC component and the DC component. The AC component of the signal is related to the pulsatile variations (for example, in the blood hemoglobin concentration) caused by the pulsation and flow of blood in the arteries. The slow-varying or unchanging DC component of signal is related to other physiological and physical properties (for example, non-pulsatile bone tissues and interstitial fluid). The first electrical signal $I_1$ may also include as an additional component a distortion from an external interference.

The DC component of the first electrical signal $I_1$ can shift the baseline of the signal waveform. For example, as shown in FIG. 4a, the baseline for the first electrical signal $I_1$ has been shifted to f(t)=+2.

Further, the second electrical signal $I_2$ generated by the second receiver 30 has a DC component that is related to the properties of the phantom material layer 40. The second electrical signal $I_2$ may also have as an additional component a distortion from an external interference. The DC component of the second electrical signal $I_2$ can also shift the baseline of the signal waveform. For example, as shown in FIG. 4b, the baseline for the second electrical signal $I_2$ has been shifted to f(t)=+1. Correspondingly, when inverted by the inverter 501, the baseline for the inverted second electrical signal $I_2'$ is shifted to f(t)=−1, as shown in FIG. 4c.

When the processor 50 adds the inverted second electrical signal $I_2'$ and the first electrical signal $I_1$ together, the interstitial fluid's contribution to the DC component of the first electrical signal $I_1$ cancels out the DC component of the second electrical signal $I_2$, and the distortions in the first and second electrical signals $I_1$, $I_2$ also cancel each other out. However, since the phantom material layer 40 does not mimic human bone tissues, the bone tissues' contribution to the DC component of the first electrical signal $I_1$ will remain and is not canceled out by a counterpart component in the second electrical signal $I_2$. As a result, following the addition process, the baseline of the blood pulse waveform remains shifted. For example, as shown in FIG. 4d, the baseline of the blood pulse waveform following the negative compensation has been shifted to f(t)=+1.

However, bone tissues of different users have different compositions, so that when the same optoelectronic sensor is used to detect the blood pulses of multiple users, each user will generate a blood pulse waveform with a different baseline shift. This can complicate any statistical and/or pathological analyses of the data. To address this problem, the processor 50 of an optoelectronic sensor according to the present disclosure may further comprise a calibrator 503, for example, as shown in FIG. 6. The calibrator 503 is configured to adjust the baselines of pulse signals generated by the processor 50, and to adjust the baseline of the blood pulse waveform determined from the pulse signals. For example, the calibrator 503 may adjust the blood pulse waveforms from different users to have a uniform zero baseline.

Optionally, the calibrator 503 may comprise a calibrating current source 80 configured to supply a calibrating current for baseline adjustment. The calibrator 503 may also comprise a second adder 5031. The second adder 5031 comprises an inverting input end, a non-inverting end and an output end. The calibrating current source 80 is coupled to the inverting input end of the second adder 5031. The output end of the first adder 502 is coupled to the inverting input end of the second adder 5031. The non-inverting input end of the second adder 5031 is grounded. The second adder 5031 is configured to output, through the output end, pulse signals that have been subject to baseline adjustment by the calibrator 503. The second adder 5031 may also comprise a current-limiting resistor R3.

Figure 4E:
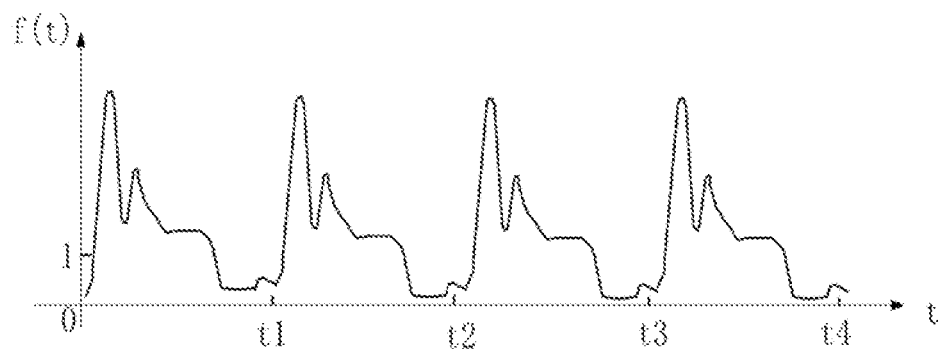
FIG. 4e shows the blood pulse signals in FIG. 4a, after a baseline adjustment.

There are no particular limitations on the current level of the calibrating current source 80, which may be adjusted to any level considered suitable by a person of ordinary skill in the art to adjust and make uniform the baseline(s) of blood pulse waveform(s) generated by the optoelectronic sensor. As an illustrative example, the reference baseline position may be set at f(t)=0, which means that the blood pulse waveform of FIG. 4d has been shifted by one (1) unit to f(t)=+1. In that case, the calibrating current source 80 may supply a current at a level that, when applied to the blood pulse waveform of FIG. 4d by the second adder 5031, is sufficient to produce the blood pulse waveform of FIG. 4e having an adjusted baseline at f(t)=0.

Processing by the calibrating current source 80 and the second adder 5031 makes it possible to correct not only a shift in the blood pulse signals generated by the processor 50, but also artifacts in the blood pulse signals, and in particular, artifacts originating from the DC component of the first electrical signal $I_1$ caused by a user's bone tissues.

Figure 5:
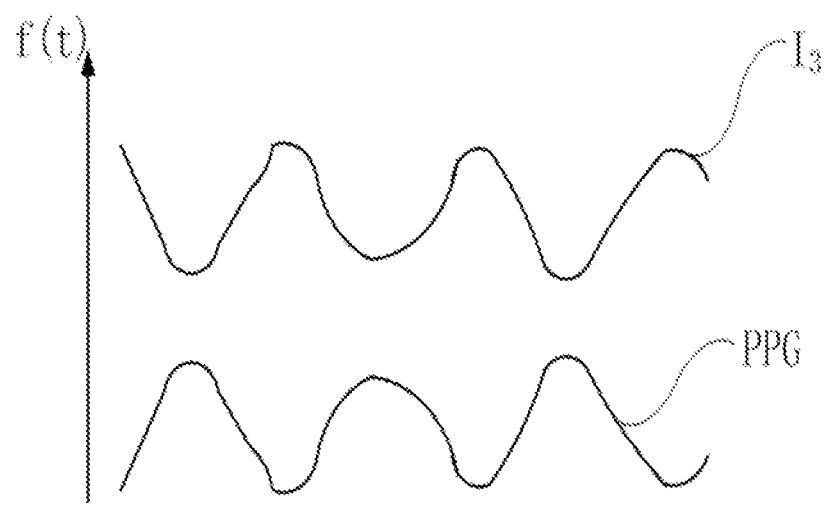
FIG. 5 is a diagram showing a correlation between blood pulse determined from an optoelectronic sensor according to the present disclosure and arterial blood volume.

When light from the light source 10 penetrates a user's skin, a portion of the light may be absorbed by different substances, including blood. The portion of the light that is not absorbed is reflected. When the heart contracts, the volume of blood in blood vessels in the skin increases. This increase corresponds to a crest in the arterial blood volume waveform $I_3$ shown in FIG. 5. When blood volume increases, light absorption by blood also increases. This reduces the amount of light reflected to the first receiver 20, and therefore, the strength of the first electrical signal $I_1$. This phenomenon is illustrated in FIG. 5. More particularly, when the arterial blood volume waveform $I_3$ is at a maximum, the blood pulse signal is at a minimum. Conversely, when the heart relaxes, the arterial blood volume waveform $I_3$ is at a minimum, the blood pulse signal is at a maximum.

When light can be easily absorbed by blood, the difference between the crest and trough of the blood pulse signal is more pronounced, which can increase the amplitude of the blood pulse waveform and facilitate pulse monitoring. Thus, in at least some embodiments of the present disclosure, the light emitted from the light source 10 is green light, red light, or infrared light. Green light may be particularly advantageous, because blood absorbs green light better than lights of other wavelengths.

In an optoelectronic sensor according to the present disclosure, the first receiver 20 and the second receiver 30 capture photo signals that are converted in an optoelectronic conversion to the first electrical signal $I_1$ and the second electrical signal $I_2$, respectively. Therefore, in at least some embodiments, the first receiver 20 and the second receiver 30 are photosensitive elements. A photosensitive element may be a photodiode, a photosensitive transistor, a photoresistor, a silicon photovoltaic cell, and the like.

In at least some embodiments, the photosensitive element is a photodiode. A photodiode comprises a photosensitive p-n junction structure. Conductivity in a photodiode is unidirectional, so that a reverse voltage is generally applied to cut off the unidirectional current. As such, when used in an optoelectronic sensor according to the present disclosure, the cathode of the photodiode is connected to the processor 50, and the anode of the photodiode is grounded. This configuration is illustrated in FIG. 6.

Figure 7:
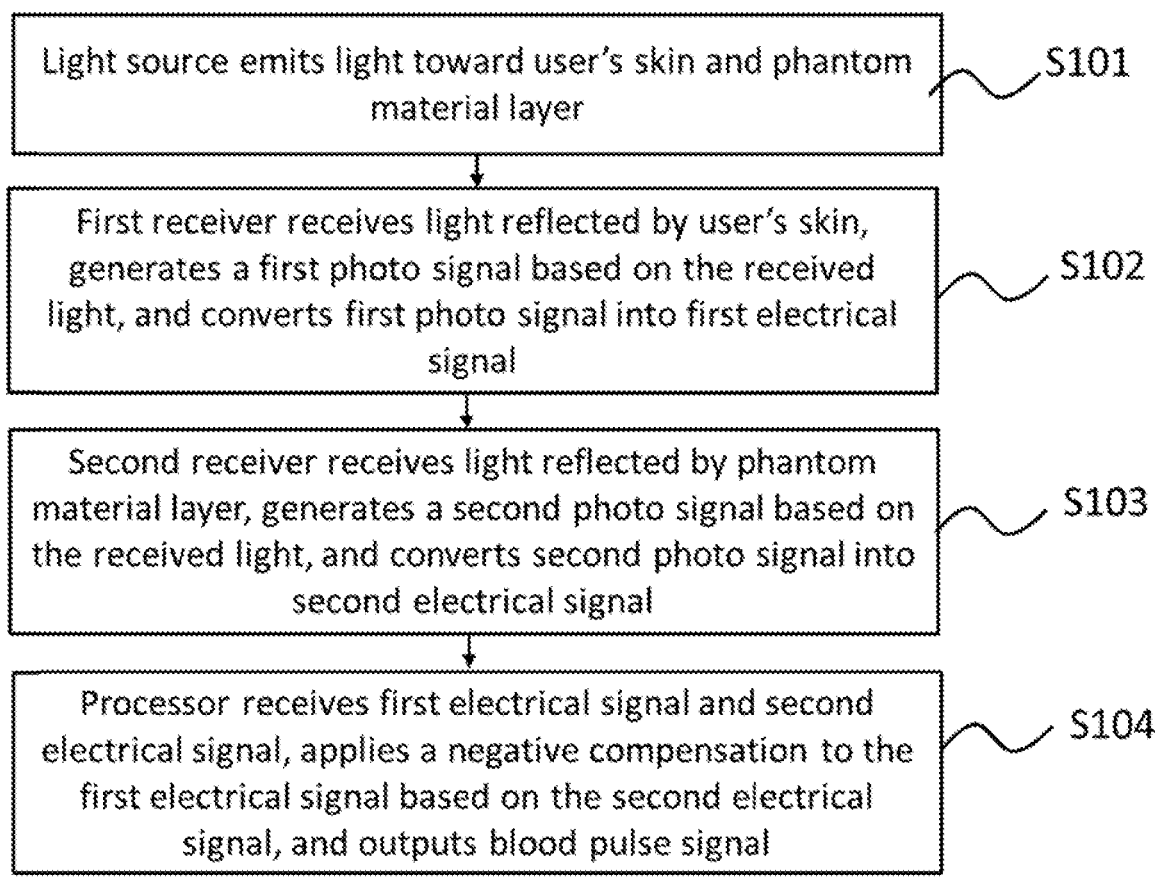
FIG. 7 shows a flowchart of a control method for an optoelectronic sensor according to the present disclosure.

An embodiment of the present disclosure also provides a control method for an optoelectronic sensor as described above. As shown in FIG. 7, the control method comprises:

Step 101 (S101): Light source 10 emits light toward a user's skin 60 and the phantom material layer 40.

For example, as shown in FIG. 3b, a first portion of the light emitted from the light source travels along a first light path (indicated by the thick solid arrow) from the light source 10 to the skin 60, and then is reflected by the skin 60 to the first receiver 20. A second portion of the light emitted from the light source 10 travels along a second light path (indicated by the dotted arrow) from the light source 10 to the phantom material layer 40, and then is reflected by the phantom material layer 40 to the second receiver 30.

Step 102 (S102): First receiver 20 receives light reflected by the skin 60 as a first photo signal, and converts the first photo signal into a first electrical signal $I_1$.

When a user uses an optoelectronic sensor 01, an external interference (for example, the user's arm movement to bring the optoelectronic sensor into a viewable position) may cause distortion in the first electric signal $I_1$. For example, as shown in FIG. 4a, the optoelectronic sensor experiences an external interference at time t1, causing an instantaneous distortion in the first electrical signal $I_1$ in the form of a blood pulse signal having abnormally large amplitude. When the external interference is removed at time t2, the amplitude of the blood pulse returns to normal.

The first electrical signal $I_1$ is obtained by an optoelectronic conversion in the first receiver 20 of light reflected from the user's skin 60. When light emitted from the light source 10 penetrates the skin 60, the light interacts with artifacts in the user's skin and blood, for example, bone tissues, interstitial fluid, and blood hemoglobin. The light reaching the first receiver 20 may therefore be modulated as a result of those interactions. Blood hemoglobin concentration has been observed to undergo pulsatile variations, whereas bone tissues and interstitial fluid generally do not change with arterial pulsatile flow. Therefore, the first electrical signal $I_1$ can be separated into at least two components: the time-varying AC component of the signal that is related to the beat-to-beat variations caused by the pulsation and flow of blood in the arteries, and the slow-varying or unchanging DC component of signal that is related to other physiological and physical properties (for example, non-pulsatile venous bone tissues and interstitial fluid).

Step 103 (S103): Second receiver 30 receives light reflected by the phantom material layer 40 as a second photo signal, and converts the second photo signal into a second electrical signal $I_2$.

An external interference that distorts the first electrical signal $I_1$ can also distort the second electrical signal $I_2$. For example, as shown in FIG. 4b, the external interference at time t1 also causes an instantaneous distortion in the second electrical signal $I_2$, in the form of an abnormal spike in the blood pulse signal. When the external interference is removed at time t2, the amplitude of the blood pulse signal returns to normal.

The second electrical signal $I_2$ is obtained by an optoelectronic conversion in the second receiver 30 of light reflected from the phantom material layer 40. When light emitted from the light source 10 impinges on the phantom material layer 40 and then reflected, the light is modulated as a result of interactions with the components making up the phantom material layer 40. The proportions of the components are fixed, so that the amount of light absorbed or reflected by the phantom material layer 40 is substantially fixed, and does not vary to any meaningful extent according to the pulsatile flow of blood in the arteries. Therefore, the second electrical signal $I_2$ may comprise predominantly a DC component.

The order of S102 and S103 is not particularly limited. S102 may be performed before S103. S103 may be performed before S102. S102 and S103 may also be performed concurrently.

Step 104 (S104): Processor 50 receives the first electrical signal $I_1$ and the second electrical signal $I_2$. The processor applies a negative compensation to the first electrical signal $I_1$ based on the second electrical signal $I_2$, and outputs a blood pulse signal.

The processor is configured to invert the second electrical signal $I_2$ (for example, as shown in FIG. 4c), and then to add the inverted second electrical signal $I_2'$ to the first electrical signal $I_1$. The processor 50 is thus configured to subtract the distortion caused by the external interference from the first electrical signal $I_1$ by an amount of distortion in the second electrical signal $I_2$. The processor 50 outputs a blood pulse signal from which the distortions caused by the external interference have been removed (for example, as shown in FIG. 4d).

When the inverted second electrical signal $I_2$ and the first electrical signal $I_1$ are added, the interstitial fluid's contribution to the DC component of the first electrical signal $I_1$ cancels out the DC component of the second electrical signal $I_2$, and the distortions in the first and second electrical signals $I_1$, $I_2$ also cancel each other out. However, since the phantom material layer 40 does not mimic human bone tissues, the bone tissues' contribution to the DC component of the first electrical signal $I_1$ will remain and is not canceled out. As a result, following the addition process, the baseline of the blood pulse signal may be shifted. For example, as shown in FIG. 4d, the baseline of the blood pulse waveform has been shifted to f(t)=+1.

The baseline shift can prevent meaningful statistical and/or pathological analyses of blood pulse signals from multiple users. This is because bone tissues of different users have different compositions, so that when the same optoelectronic sensor is used to detect the blood pulses of multiple users, each user will generate a blood pulse waveform with a different baseline shift.

The control method for an optoelectronic sensor according to the present disclosure may therefore also comprise a calibration step, during which a calibrator 503 adjusts the baselines of blood pulse signals generated by the processor 50.

The calibrator 503 may comprise a calibrating current source 80 and a second adder 5031. The calibrating current source 80 supplies a current at a level that, when applied to the blood pulse signal by the second adder 5031, is sufficient to adjust the baseline of the blood pulse signal to the appropriate reference position. Processing by the calibrating current source 80 and the second adder 5031 makes it possible to correct not only a shift in the blood pulse signals generated by the processor 50, but also artifacts in the blood pulse signals, and in particular, artifacts originating from the DC component of the first electrical signal $I_1$ caused by a user's bone tissues.

Another embodiment of the present disclosure provides a pulse monitor comprising an optoelectronic sensor as described above. The pulse monitor can realize the same construction and advantages as an optoelectronic sensor described above.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An optoelectronic sensor for determining a blood pulse, comprising:
   a base substrate;
   a light source on the base substrate;
   a first receiver on the base substrate and on one side of the light source;
   a second receiver on the base substrate and on a different side of the light source from the first receiver;
   a phantom material layer facing a light-emitting side of the light source and at least partially overlapping with the second receiver; and
   a first light-blocking layer on a surface of the phantom material layer distal to the second receiver,
   wherein:
   the first receiver is configured to generate a first photo signal based on a light emitted from the light source and reflected from a skin of a user, and convert the first photo signal into a first electrical signal;
   the second receiver is configured to generate a second photo signal based on a light emitted from the light source and reflected from the phantom material layer, and convert the second photo signal into a second electrical signal;
   the optoelectronic sensor is configured to, in determining the blood pulse, apply a compensation factor to the first electrical signal based on the second electrical signal;
   the phantom material layer is a gel material including salt, oil and gelling agent, which is configured to mimic electrical properties of the skin of the user to modulate the light emitted from the light source;

the phantom material layer absorbs or reflects substantially fixed amount of light emitted from the light source;

the first light-blocking layer is configured to prevent the light emitted from the light source from transmitting through the phantom material layer to the skin of the user; and the optoelectronic sensor further includes a processor coupled to the first receiver and the second receiver, wherein:

the processor is configured to invert the second electrical signal, and add the first electrical signal and the inverted second electrical signal, so as to generate a blood pulse signal for determining the blood pulse; and the inverted second electrical signal defines the compensation factor.

2. The optoelectronic sensor according to claim 1, wherein the processor is further configured to adjust a baseline of the blood pulse signal generated by the processor, and to adjust a baseline of a blood pulse waveform determined from the blood pulse signal.

3. The optoelectronic sensor according to claim 1, wherein the phantom material layer faces an entirety of a light-receiving surface of the second receiver.

4. The optoelectronic sensor according to claim 1, wherein a width of the phantom material layer is less than half of an overall width of the optoelectronic sensor.

5. The optoelectronic sensor according to claim 1, further comprising a transparent housing containing the light source, the first receiver, the second receiver, and the phantom material layer, wherein:

a first separation distance separates a light-receiving surface of the first receiver and a side of the transparent housing facing the light-receiving surface of the first receiver;

a second separation distance separates a light-receiving surface of the second receiver from a side of the transparent housing facing the light-receiving surface of the second receiver; and the first separation distance is larger than the second separation distance.

6. The optoelectronic sensor according to claim 5, wherein:

the phantom material layer is on a side of the transparent housing facing the second receiver; and the first light-blocking layer is between the phantom material layer and the transparent housing.

7. The optoelectronic sensor according to claim 1, wherein:

the light source is between the first receiver and the second receiver; and the light source, the first receiver and the second receiver are arranged substantially along a same direction.

8. The optoelectronic sensor according to claim 1, wherein the light source is at a halfway point between the first receiver and the second receiver.

9. The optoelectronic sensor according claim 1, further comprising a second light-blocking layer on at least one side surface of the light source facing one of the first receiver and the second receiver.

10. The optoelectronic sensor according to claim 1, wherein:

the phantom material layer has a thickness of from 1 to 2 millimeters.

11. The optoelectronic sensor according to claim 1, wherein the phantom material layer is formed by solidifying a liquid mixture comprising a gelling agent, deionized water, saline solution, and oil into a gel material.

12. The optoelectronic sensor according to claim 1, wherein at least one of the first receiver and the second receiver is a photosensitive element.

13. The optoelectronic sensor according to claim 1, wherein at least one of the first receiver and the second receiver is a photodiode.

14. A method for determining a blood pulse using an optoelectronic sensor comprising a base substrate, a light source on the base substrate, a first receiver on the base substrate, a second receiver on a base substrate and on a different side of the light source from the first receiver, a phantom material layer facing a light-emitting side of the light source and at least partially overlapping with the second receiver, the method comprising:

generating a first photo signal based on a light emitted from the light source and reflected by a skin of a use, converting the first photo signal into a first electrical signal, generating a second photo signal based on a light emitted from the light source and reflected by the phantom material layer, converting the second photo signal into a second electrical signal, and applying a compensation factor to the first electrical signal based on the second electrical signal to determine a blood pulse, wherein the phantom material layer is a gel material including salt, oil and gelling agent, configured to mimic electrical properties of the skin of the user to modulate the light emitted from the light source;

the phantom material layer absorbs or reflects substantially fixed amount of light emitted from the light source;

and the second electrical signal is processed to obtain the compensation factor.

15. The method according to claim 14, wherein the applying of the compensation factor comprises:

inverting the second electrical signal, and adding the inverted second electrical signal to the first electrical signal, so as to generate a blood pulse signal for determining the blood pulse, and wherein the inverted second electrical signal defines the compensation factor.

16. The method according to claim 15, further comprising: adjusting a baseline of the blood pulse signal, and adjusting a baseline of a blood pulse waveform determined from the blood pulse signal.

17. A pulse monitor comprising the optoelectronic sensor according to claim 1.

* * * * *